US008216790B2

(12) United States Patent
Fetissov et al.

(10) Patent No.: US 8,216,790 B2
(45) Date of Patent: Jul. 10, 2012

(54) METHOD OF DIAGNOSING NEUROPSYCHIATRIC DISEASES, EATING DISORDERS OR METABOLIC DISEASES

(75) Inventors: Serguei Fetissov, Montigny (FR); Pierre Dechelotte, Rouen (FR); Maria Hamze-Sinno, Rouen (FR); Danièle Gilbert, Sainte-Pierre de Varengeville (FR)

(73) Assignees: Serguei Fetissov, Montigny (FR); Pierre Dechelotte, Rouen (FR)

( * ) Notice: Subject to any disclaimer, the term of this patent is extended or adjusted under 35 U.S.C. 154(b) by 212 days.

(21) Appl. No.: 12/444,340

(22) PCT Filed: Oct. 3, 2007

(86) PCT No.: PCT/FR2007/001617
§ 371 (c)(1),
(2), (4) Date: Aug. 13, 2009

(87) PCT Pub. No.: WO2008/040882
PCT Pub. Date: Apr. 10, 2008

(65) Prior Publication Data
US 2009/0305434 A1    Dec. 10, 2009

(30) Foreign Application Priority Data
Oct. 3, 2006 (FR) ..................................... 06 08664

(51) Int. Cl.
*G01N 33/53* (2006.01)
*G01N 33/557* (2006.01)
*G01N 33/564* (2006.01)
(52) U.S. Cl. ............................ 435/7.1; 436/513; 436/517
(58) Field of Classification Search .......................... None
See application file for complete search history.

(56) References Cited

U.S. PATENT DOCUMENTS
6,635,479 B1    10/2003    Sutcliffe et al.

FOREIGN PATENT DOCUMENTS
WO    WO-2005/058961 A    6/2005

OTHER PUBLICATIONS

Schlosser M et al. In insulin-autoantibody-positive children from the general population, antibody affinity identifies those at high and low risk. Diabetologia, 2005; 48:1830-1832.*
Fetissov So et al. Autoantibodies against neuropeptides are associated with psychological traits in eating disorders. Proc Natl Acad Sci USA, 2005; 103(41):14865-14870.*
Comin, Romina, et al.: "High affinity of anti-GM(1) antibodies is associated with disease onset in experimental neuropathy", Journal of Neuroscience Research, vol. 84, No. 5, Jul. 31, 2006, pp. 1085-1090, XP009088528, Wiley-Liss, US, ISSN: 0360-4012.
Dicou, E., et al.: "Natural autoantibodies against the nerve growth factor in autoimmune diseases", Journal of Neuroimmunology, vol. 47, No. 2, Sep. 1993, pp. 159-167, XP009088532, ISSN: 0165-5728.
Shaw, G., et al.: "alpha-MSH and neurofilament M-protein share a continuous epitope but not extended sequences. An explanation for neurofibrillary staining with alpha-MSH antibodies", FEBs Letters, vol. 181, No. 2, Feb. 25, 1985, pp. 343-346, XP002448115, ISSN: 0014-5793.
Fetissov, S. O., et al.: "Autoantibodies against alpha-MSH, ACTH, and LHRH in anorexia and bulimia nervosa patients", Proceedings of the National Academy of Sciences of the United States of America, vol. 99, No. 26, Dec. 24, 2002, pp. 17155-17160, XP009086396, ISSN: 0027-8424.
Fetissov, S. O., et al.: "Aggressive behavior linked to corticotropin-reactive autoantibodies", Biological Psychiatry, vol. 60, No. 8, Oct. 15, 2006, pp. 799-802, XP005697106, ISSN: 0006-3223.
Fetissov, Serguei O., et al.: "Autoantibodies against appetite-regulating peptide hormones and neuropeptides: Putative modulation by gut microflora", Nutrition Apr. 2008, vol. 24, No. 4, pp. 348-359, XP022510832, ISSN: 0899-9007.
Abstract of Fetissov, S. et al. Autoimmune component in anorexia and bulimia nervosa. SSIB 11th Annual Meeting, Groningen, The Netherlands (2003) pp. 253-262; cited in Abstracts—Society for the Study of Ingestive Behavior: Annual Meeting Jul. 15-19, 2003, Univ. of Groningen, Haren, The Netherlands; Appetite 40 (2003), pp. 313-374.
Adamczyk, M. et al., Application of Surface Plasmon Resonance toward Studies of Low-Molecular-Weight Antigen-Antibody Binding Interactions. Methods (2000) 20:319-328.
Andlin-Sobocki, P. et al. Cost of disorders of the brain in Europe. European Journal of Neurology (2005) 12 Suppl 1:1-27.
Bendtzen K. et al., High-avidity autoantibodies to cytokines. Trends Immunology Today 19:5, 209-211,1998.
Black, III, J. et al., Analysis of Hypocretin (Orexin) Antibodies in Patients with Narcolepsy. Sleep (2005) vol. 28, No. 4.
Choi, YH. et al., Melanocortin receptors mediate leptin effects on feeding and body weight but not adipose apoptosis. Physiology & Behavior (2003) 79:795-801.
Cone, R. et al. Anatomy and regulation of the central melanocortin system. Nature Neuroscience (May 2005) 8:5, 571-578.

(Continued)

*Primary Examiner* — Elizabeth C Kemmerer
*Assistant Examiner* — Kimberly A Ballard
(74) *Attorney, Agent, or Firm* — Harness, Dickey & Pierce, P.L.C.

(57) ABSTRACT

The application relates to a method of diagnosing neuropsychiatric diseases, eating disorders and/or metabolic diseases, which comprises: (i) measuring the affinity and/or the avidity of antibodies, derived from a biological sample, directed against a biological molecule involved in homeostatic regulation and/or in motivational behavior and/or in emotion; (ii) comparing the affinity value obtained with a control value.

1 Claim, 5 Drawing Sheets

OTHER PUBLICATIONS

Coquerel, Q. et al., Intestinal inflammation influences α-MSH reactive autoantibodies: Relevance to food intake and body weight. Psychoneuroendocrinology (2011), doi: 10.1016/j.psyneuen.2011.05/008.

Corcos, M. et al., Bulimia nervosa and autoimmunity. Psychiatry Research (1999) 87:77-82.

De Lecea, L. et al., The hypocretins: hypothalamus-specific peptides with neuroexcitatory activity. Proc. Natl. Acad. Sci. USA (Jan. 1998) 95:322-327.

De Wied, D. et al., Effects of Peptide Hormones on Behavior. Frontiers in Neuroendocrinology (1969) pp. 97-140.

Deloumeau, A. et al., Increased Immune Complexes of Hypocretin Autoantibodies in Narcolepsy. PLoS ONE (Oct. 2010) 5:10, 1-7.

Dicou, E. et al., Evidence that natural autoantibodies against the nerve growth factor (NGF) may be potential carriers of NGF. Journal of Neuroimmunology, 75:200-203, 1997.

Dimitrov, J. et al., Important parameters for evaluation of antibody avidity by immunosorbent assay. Analytical Biochemistry (2011) 418:149-151.

Fan, W. et al., Role of melanocortinergic neurons in feeding and the agouti obesity syndrome. Nature (1997) 385:165-168.

Fetissov, S. et al., Aggressive Behavior Linked to Corticotropin-Reactive Autoantibodies. Biol Psychiatry (2006) pp. 799-802.

Garcia, F. et al., Autoantibodies reacting with vasopressin and oxytocin in relation to cortisol secretion in mild and moderate depression. Progress in Neuro-Psychopharmacology & Biological Psychiatry (2011) 35:118-125.

Haller, J. et al., Mechanisms differentiating normal from abnormal aggression: glucocorticoids and serotonin. European Journal of Pharmacology (2005) 526:89-100.

Hamze Sinno, M. et al., Regulation of feeding and anxiety by α-MSH reactive autoantibodies. Psychoneuroendocrinology (2009) 34:140-149.

Heisler, L. et al., Activation of Central Melanocortin Pathways by Fenfluramine. Science (2002) 297:609-611.

Hillebrand, J. et al., Neuropeptides, food intake and body weight regulation: a hypothalamic focus. Peptides (2002) 23:2283-2306.

Hökfelt T. et al., Neuropeptides: opportunities for drug discovery. Lancet Neurology (Aug. 2003) 2:463-472.

Hökfelt T. et al., NPY and its involvement in axon guidance, neurogenesis, and feeding. Nutrition 24 (2008) pp. 860-868.

Karaiskos, D. et al., Psychopathological and personality features in primary Sjögren's syndrome—associations with autoantibodies to neuropeptides. Rheumatology (2010) 49:1762-1769.

Lardone, R. et al., Anti-GM$_1$ IgG antibodies in Guillain-Barré syndrome: fine specificity is associated with disease severity. J Neurol Neurosurg Psychiatry (2010) 81:629-633.

Lawrence, C.B. et al., Anorexic But Not Pyrogenic Actions of Interleukin-1 are Modulated by Central Melanocortin-3/4 Receptors in the Rat. Journal of Neuroendocrinology (2001) 13:490-495.

Leibowitz, S. et al., Hypothalamic serotonin in control of eating behavior, meal size, and body weight. Biological Psychiatry (1998) 44:851-864.

Marks, D. et al., Role of the central melanocortin system in cachexia. Cancer Res (2001) 61:1432-1438.

Marsh, D. et al., Response of melanocortin-4 receptor-deficient mice to anorectic and orexigenic peptides. Nature Genetics (Jan. 1999) 21:119-122.

Meguid, M. et al., Hypothalamic dopamine and serotonin in the regulation of food intake. Nutrition (2000) 16:843-857.

Obici, S. et al., Central melanocortin receptors regulate insulin action. Journal of Clinical Investigation (Oct. 2001) 108:1079-1085.

Pedrazzini, T. et al., Neuropeptide Y: the universal soldier. Cell Mol Life Sci (2003) 60:350-377.

Pinckard, R. et al., Equilibrium dialysis and preparation of hapten conjugates. In: Weir DM, Editor. Handbook of experimental immunology. Oxford: Blackwell Science. (1978) pp. 17.11-17.23.

Pullen, G. et al., Antibody avidity determination by ELISA using thiocyanate elution. Journal of Immunological Methods (1986) 86:83-87.

Rich, R. et al., Advances in surface plaimon resonance biosensor analysis. Current Opinion in Biotechnology (2000) 11:54-61.

Scantamburlo, G. et al., AVP- and OT-neurophysins response to apomorphine and clonidine in major depression. Psychoneuroendocrinology (2005) 30:839-845.

Seeley, R. et al., Melanocortin receptors in leptin effects. Nature (Nov. 1997) 390:349.

Sewards, T. et al., Fear and power-dominance motivation: proposed contributions of peptide hormones present in cerebrospinal fluid and plasma. Neuroscience and Biobehavioral Reviews (2003) 27:247-267.

Siljander, H. et al., Role of insulin autoantibody affinity as a predictive marker for type 1 diabetes in young children with HLA-conferred disease susceptibility. Diabetes Metab Res Rev (2009) 25:615-622.

Swaab, D. Neuropeptides in hypothalamic neuronal disorders. International Review of Cytology (2004) 240:305-375.

Tanaka, S. et al., Detection of autoantibodies against hypocretin, hcrtrl, and hcrtr2 in narcolepsy: anti-Hcrt system antibody in narcolepsy. Sleep (2006) 29:633-638.

Vuignier, K. et al., Drug-protein binding: a critical review of analytical tools. Anal Bioanal Chem (2010) 398:53-66.

Walsh, B. Fluoxetine after weight restoration in anorexia nervosa: a randomized controlled trial. JAMA (2006) vol. 295, No. 22, pp. 2605-2612.

Zhang, Y. et al., Circumventing central leptin resistance: Lessons from central leptin and POMC gene delivery. Peptides (2006) 27:350-364.

Zorrilla E. et al., Vaccination against weight gain. Proc Natl Acad Sci U.S.A. (2006) vol. 29, No. 35, pp. 13226-13231.

* cited by examiner

METHOD OF DIAGNOSING NEUROPSYCHIATRIC DISEASES, EATING DISORDERS OR METABOLIC DISEASES

CROSS-REFERENCE TO RELATED APPLICATIONS

This application is a National Phase Entry of International Application No. PCT/FR2007/001617, filed Oct. 3, 2007, which claims priority to French Patent Application No. 06/08664, filed Oct. 3, 2006, both of which are incorporated herein by reference.

BACKGROUND

1. Technical Field of the Invention

The present invention relates to the field of diagnosing or prognosticating neuropsychiatric diseases (hereinafter ND), eating disorders (hereinafter ED) or metabolic diseases. Eating disorders belong to motivational behavior disorders (MBD). The present invention also relates to the treatment of eating disorders. More particularly, the invention relates to a method for diagnosing or prognosticating NDs or EDs by measuring the affinity of a patient's autoantibodies for the biological molecule. The development of such invention follows the finding by the inventors of the psychological part in homeostasis and behavior of autoantibodies directed against certain biological molecules in particular neuropeptides, hormones and neurotransmitters.

"Autoantibodies" (hereinafter AutoAbs), in the sense of the present invention, means immunoglobulin capable of binding with molecules belonging to an organism producing said immunoglobulin. Such AutoAbs react against the "self". An individual's self is defined as the assembly of molecules resulting from the normal expression of his or her genome. Such AutoAbs are naturally produced in the organism, i.e. they are not administrated by a passive immunization with human or animal original serum or with compounds containing monoclonal or recombinant antibodies. Such AutoAbs are not stimulated by an active immunization in which antigen is represented by neuropeptides, hormones or fragments thereof.

"Motivational behavior" means any behavior which serves to maintain the homeostasis of the organism by protecting it against external stresses or noxious modifications in environmental conditions. The motivational behavior is essentially involved in the regulation of nutrient intakes and is also used for extending life through reproduction. More exactly, motivational behavior includes the following behaviors: dietary intake, water intake, reproduction behavior which includes sexual and maternal or paternal behavior, defense or aggression behavior, exploration behavior, storage behavior and the behavior aiming at maintaining the body temperature and sleep. Such behaviors are regulated and integrated in a region of the brain called hypothalamus, since the alteration in the mechanism of a behavior also affects the others. In addition, strong connections of the hypothalamus with regions of the brain which are responsible for the emotional response, more particularly the rhinencephalon, also involve emotional disorders when one or several mechanisms of the motivational behavior is/are affected.

Some NDs or MBDs can be characterised by the presence of somatic and psychiatric symptoms. This can be explained by the neuro-anatomic interactions and also neuro-chemical interactions. Some NDs or MBDs can be distinguished, in which the psychiatric component is substantially characterised by symptoms involving modifications in the motivational behavior and/or emotion. Among NDs or MBDs with a strong psychiatric component, more particularly EDs, anxiety, depression, social phobia, delinquency, sexual disorders and sleep disorders can more particularly be mentioned.

Other NDs or MBDs can be characterised by the dominant alteration of the somatic component. This is most often revealed as pains which can be transitory or chronic such as for example in fibromyalgy or the irritable bowel syndrome. An important group of NDs or MBDs with strong somatic or psychiatric components is formed by EDs where somatic symptoms are associated with nutrient disorders. Undernutrition can more particularly be cited in anorexia nervosa or the case of obesity in bulimic behaviors.

In EDs, the psychiatric component can be characterised by symptoms affecting the motivational behavior and/or emotion such as dietary intake disorders and anxiety. The mechanisms implied in some NDs or EDs can also be involved in the occurrence of metabolic complications which can justify the inclusion of some metabolic diseases in the field of the invention, more particularly obesity for example, obesity due to excessive caloric intake, complications caused by obesity, type II diabetes and the metabolic syndrome.

2. Prior Art

Today, MBDs are an important public health issue, since the prevalence of anorexia nervosa is estimated between 0.3% to 0.7%, that of bulimia at about 3 to 5% in women, since EDs affect men 10 to 20 times less frequently. This would thus represent over 100,000 anorectic persons and over one million bulimic persons in France. Mortality due to anorexia nervosa can reach 10%. This affection is thus clearly extremely serious.

Besides, the persistence of pathologic symptoms and the frequent relapses noted in all the forms of EDs significantly reduce the quality of life of the affected persons. Other NDs and MBDs than those mentioned above are also extremely frequent in the world. As an example, mood disorders and anxiety affect altogether over 60 million persons in Europe (Andin-Sobocki and al., 2005).

So far, the origin of NDs and EDs or MBDs remains unknown or at least extremely argued about. On the other hand, no biological marker of such NDs or EDs is known which does not make it possible to have a specific diagnostic of NDs, EDs or MBDs. This is the reason why the present diagnosis of NDs, EDs and MBDs is purely symptomatic which is not always true. As regards the field of therapy, there is no etiologic treatment of EDs and clinical studies show the failures of traditionally prescribed drugs for NDs for example that on the antidepressive drug fluoxetine (Walsh and al., 2006).

In spite of such diagnosis and therapeutic problems, experimental research has made significant progress in the understanding of the molecular basis of motivational of behavior and emotion. Studies on the animal models showed the important part of neuropeptides and hormones, molecules synthesized by neuronal cells and endocrine cells respectively, in the physiological regulation of the motivational behavior and emotion (de Wied, 1969). This research made it possible to establish that some neuropeptides/hormones are preferably involved in motivational behavior, emotion or homeostasic functions (Hökfelt and al., 2003; Swaab, 2004). It was shown, for example, that vasopressin plays a key role in social dominance, fear and depression (Sewards and Sewards, 2003; Scantamburlo and al., 2005), ocytocin in inter-individual relationship and pain, adrenocorticotropic hormone in aggression, memory and depression (Haller and al., 2005), hypocretin in dietary intake and sleep (De Lecea and al., 1998), and neuropeptide Y in reproduction and dietary intake (Pedrazzini and al., 2003).

As regards energetic homeostasis, studies showed that the alpha-melabocyte/stimulating hormone (α-MSH or a-MSH or alpha-MSH) plays a key role in the regulation of eating behavior (Fan and al., 1997; Cone, 2005) and is an anorexiant. Besides, AgRP (Agouti related protein) plays the role of an antagonist of α-MSH through its competition for the same receptor of the melanocortin type, the stimulation of which by α-MSH appears as the final common channel to the induction of saturation (Cone, 2005). The other transmitters which are capable of modifying the dietary intake, for example monoamines (Leibowitz and Alexander, 1998; Meguid and al., 2000) interact at several levels with the system of melanocortin. Thus, this final channel appears to be critical for anorexiant actions of serotonin (Heisler and al., 2002), leptin (Seeley and al., 1997; Marsh and al., 1999; Choi and al., 2003; Zhang and Scarpace, 2006) insulin (Obici and al., 2001), pro-inflammatory cytokine (Lawrence and Rothwell, 2001; Marks and al., 2001), but also for the orexigenic action of ghrelin via neuropeptide Y (NPY) and AgRP. However, in spite of the progress of fundamental research, the pathologic mechanism involving neuropeptides in the pathogenesis of NDs and MBDs and more particular EDs is not clear.

A new hypothesis relating to the pathologic mechanism in which NDs or MBDs or EDs originate has recently been proposed (Fetissov and Hökfelt, 2003). According to this assumption, NDs or MBDs and EDs could be caused by the presence of circulant autoantibodies directed against neuropeptides/hormones more particularly implied in the regulation of the motivational behavior and emotion, more particularly alpha-melanocyte stimulating hormone (α-MSH), adrenocorticotropic hormone (ACTH), the luteinizing hormone releasing hormone (LHRH), ocytocin and vasopressin (Fetissov and al., 2002; Fetissov and al., 2005). Recent studies also show the presence of autoantibodies against hypocretin neuropeptide during sleep disorders but in a way which is not different from that of control patients (Black and al., 2005; Tanaka et al., 2006). Other works showed in controlled patients and bulimic patients the presence of autoantibodies directed against the molecules which, through their chemical structure, do not belong to neuropeptides, but are involved in neurotransmission such as serotonin and dopamine as well as against the enzyme responsible for the synthesis of noradrenalin, dopamine β-hydroxylase (Corcos and al., 1999).

The presence of such autoantibodies in patients revealed in these works could suggest a pathological mechanism for NDs or MBDs and EDs, for example through the neutralization of messenger molecules. However, such antibodies have also been detected in sound persons, sometimes with higher titers than in sick persons (Corcos and al., 1999; Black and al., 2005; Fetissov and al., 2005). Thus, the detection of such autoantibodies for the diagnosis of NDs or EDs and MBDs does not seem to be a reliable method. Thus, so far, the real involvement of such autoantibodies in the etiopathogenia of NDs or MBDs and EDs is still not solved. Thus, there is a need for reliable and reproducible methods for diagnosing and prognosticating NDs or MBDs and EDs.

SUMMARY OF THE INVENTION

The present invention is based on the finding that in a human being, some properties of the autoantibodies directed against neuropeptides/hormones are responsible for their pathogenic actions and can thus be used for the diagnosis, prognosis and therapeutics of NDs, MBDs, EDs and/or metabolic diseases. The development of this invention follows the finding by the inventors of the role in homeostasis and the behavior of autoantibodies directed against some biological molecules more particularly neuropeptides, hormones and neurotransmitters. In particular, the inventors showed that metabolic diseases, NDs, MBDs, EDs more particularly anorexia and bulimia are connected to affinity and/or avidity of autoantibodies directed against a biological molecule.

"Biological molecule", in the sense of the present invention, means any molecule produced by a human organism, more particularly neuropeptides, hormones or neurotransmitters. "Affinity", in the sense of the present invention, means the force with which a unique antibody site binds to only one epitope of the antigen. The affinity of antibodies is conceived as the resultant of the attractive and repulsive forces established between the antibodies and the homologous epitopes of the corresponding antigen or with haptenes. The affinity and the valence of an antibody can be determined by an equilibrium dialysis. The calculation of the affinity of an antibody site requires using either a monovalent antigen or an isolated antigenic determinant (or an haptene).

Generally speaking, antibodies which loosely combine with the antigen and easily dissociate are called "low affinity" antibodies ($10^4$ to $10^5$ l/mol), whereas the antibodies strongly fixing are called "high affinity" antibodies (from $10^8$ to $10^{11}$ l/mol). The affinity depends on the degree of stereo-chemical complementarity between the combination sites of the antibodies and the antigenic determinants.

"Avidity or functional affinity", in the sense of the present invention, means the global binding force of an antibody molecule for an antigen or a particle. This force can depend on the paratope/epitope affinity, of the valence of the antibody which represents the number of binding sites per antibody molecule (for example 2 for one IgG, 10 for one IgM) and/or the valence of the antigen. The avidity of an antibody for an antigen depends on the affinity of each one of the antibody sites for the various antigenic determinant and is greater than the sum of such affinities in the case of multivalent antigens and antibodies, which is a reflection that all the bonds between the antigen and the antibody must be broken at the same time for both molecules to be separated.

As any antibody binds to its specific antigen or to several antigens with some affinity and since in the case where the antigen is represented by a messenger molecule such as a hormone or a neuropeptide, the binding affinity will determine the role of the antibody either as an antigen blocking substance or as an antigen carrier substance. The measure of the affinity of autoantibodies to peptides involved in the regulation of motivational behavior and emotion brings diagnosing values on the endogen functional condition of the corresponding peptidergic systems. As the blocking effect of antigen by its antibody is well known, the carrier effect of some messenger molecules has been suggested by a few publications such as Bendtzen K. and al. High-avidity autoantibodies to cytokinees. Trends immunology today 19:5, 209-211, 1998 and Dicou E. and Nerriere V., Evidence but natural antibodies against the nerve growth factor (NGF) may be potential carriers of NGF, Journal of Neuroimmunology, 75:1-2, 200-203,1997.

A recent document shows that the complex of the growth hormone with the soluble receptor thereof has an agonist effect which is stronger than the growth hormone alone, a phenomenon which can be applied to hormone or neuropeptides complexes with the corresponding autoantibodies thereof, since the formation of autoantibodies-peptide or receptor-peptide complexes involves the same non covalent chemical forces, which are responsible for the affinity of the peptide for the receptor or for the autoantibody. However, the measure of the affinity of the autoantibodies directed against the peptides involved in the regulation of motivational behavior, mood and emotion has not been reported so far. However, the measure of the affinity of some autoantibodies is provided for the diagnosis of conventional autoimmune diseases; the affinity of the autoantibodies against insulin in type 1 diabetes, as described in Schlosser M. and al., In insulin-autoantibody-positive children from the general population, antibody affinity identifies those at high and low risk. Diabetologia 48: 1830-1832, 2005. Another publication shows that the affinity of the autoantibodies directed against ganglioside GM1 which is a glycoshpinglipid, because of its chemical structure, present in the nuclear envelope can be associated with a neuropathy of the Guillain-Barré syndrome type, as described in Comin R. and al., High affinity of anti GM1 antibodies is associated with disease onset in experimental neuropathy. J. Neurosci. Res. 84:5, 1085-90, 2006.

The fact that the measure of affinity of the autoantibodies directed against neuropeptides/hormones involved in the regulation of motivational behavior, mood and emotion has not bee used yet can be explained by the recent evidencing of the autoantibodies against a limited number of such messenger molecules. As a matter of fact, the presence in human beings of autoantibodies has been reported for a-MSH, MCH, ACTH, LHRH, vasopressin and ocytocin by recent publications like Fetissov and al. 2002 and 2005. This is also true for hypocretin (orexin) by Black J L 2005 and Tanaka S 2006.

Apart from these peptides, the inventors recently identified the presence in human beings of autoantibodies directed against several neuropeptides/hormones involved in the regulation of motivational behavior, mood and emotion which, as far as they know, had not been the subject of prior art publications. Autoantibodies directed against leptin, ghrelin, AgRP, (Agouti-related peptide), NPY (Neuropeptide Y), PYY (Peptide YY), galanin, CRH (corticotrophin-releasing hormone) and growth hormone. FIG. 3 appended herewith shows, in sound persons, serum concentrations (average±SE) of autoantibodies of the IgG and IgA types directed against fourteen neuropeptide/hormones measured with the direct ELISA technique described hereinunder for a-MSH. The inventors also identified autoantibodies against such neuropeptide/hormones in rats. The specificity of each serum autoantibody to bind with the neuropeptide/hormone has been checked by the pre-absorption of the serum with synthetic neuropeptide/hormones.

A first aspect of the present invention relates to a method of diagnosing neuropsychiatric diseases, eating disorders and/or metabolic diseases including the steps consisting in:
(i) measuring the affinity and/or the avidity of antibodies, derived from a biological sample, directed against the biological molecule involved in homeostasic regulation and/or in motivational behavior, and/or in emotion;
(ii) comparing the affinity value obtained with a control value.

"Control value" means, in the sense of the present invention, a known value of the affinity or the avidity which can be either (i) a reference value of the affinity and/or avidity of autoantibodies in a sound person or (ii) a reference value of the affinity and/or avidity of autoantibodies in a person suffering from an ND, MBD, ED or a given metabolic disease. "Biological sample" means blood, serum, saliva or any sample taken from a patient liable to contain immunoglobulins, preferably blood, serum and saliva.

The measure of affinity and/or avidity constants can be made through methods which are well known to the persons skilled in the art and which are in addition described in Pinckard's manual (Pinckard, 1978). For measuring affinity, the equilibrium dialysis method can more particularly be cited. Such method makes it possible to measure the quantity of antibodies in a solution. This method can be used in the case of small size antigens (less than 100,000 Da), with the latter having to be able to go through the dialysis diaphragm, whereas the antibodies cannot scatter because of their dimensions.

Both partners are placed in different compartments and the antigen, which can be previously marked more particularly by a radioactive isotope, is let to scatter. When the equilibrium is reached, the antigen is quantified in each of the two compartments. When applying the mass action law which is well known to the persons skilled in the art (Pinckard, 1978), the equilibrium association constant can be determined.

For the measure of avidity and affinity, an elution test, with the modified ELISA technique (Enzyme Linked Immunosorbent Assay) can be used with the antigen being in a solid phase and the antibody being in a liquid phase. A dissociation agent, for example a chaotropic agent, more particularly isothiocyanate $NH^4SCN$, is used for dissociating the antigen/antibody complexes. Since the low avidity antibodies are eluted by lower concentrations of the dissociation agent, the concentration for eluting 50% of the linked antibodies (avidity index) is a correct measure of the average avidity of the analyzed antibodies (Pullen G R J. Immunol Methods, 1986, 86:83-7).

A privileged method for determining the affinity and/or the avidity of an antibody is based on the utilization of optical biosensors making it possible to measure the molecular interactions in real time, by a surface plasmon resonance analysis. The resonance of surface plasmon is an optical method using the surface electromagnetic waves for sampling the variations in mass, index and thickness occurring at the interface between a metal and a dielectric. This technique does not require the marking of biomolecules which could denature them.

The resonance conditions are influenced by the material absorbed on the metallic film or more exactly a linear relationship has been found between the resonance energy and the mass concentration of biological molecules such as proteins, DNA or carbohydrates. The signal of the Surface Plasmon Resonance (SPR) expressed in resonance units (RU) is in fact an indirect measurement of the mass concentration at the surface of the chip. This means that the association and dissociation of the antibody/antigen complex can be noted and that subsequently the constants, more particularly the equilibrium constant can be calculated.

In a preferred embodiment of the invention, the affinity and/or the avidity is determined by measuring the surface plasmon resonance according to the BIAcore (trade mark) technology (Rich and Myszka, 2000). The Biacore (trade mark) instrument aims at visualizing, in real time, interactions between non marked biomolecules associated with a fluid system, which makes it possible to have a flux of various solutions with a continuous rate pass on the chip. One of the reagents, for example the antigen, is specifically retained on a matrix called "sensor chip". The Biacore (trade mark) chips, which are most often used, are composed of a glass support covered with gold functionalized by a biopolymer, carboxymethylated dextran. The antibodies are injected with a constant rate by a microfluidic circuit in contact with the interface. The mass variation induced by the association or the dissociation of the complexes modify the refringence of the medium and shift the position of the resonance angle. The recording of the variation in the resonance angle makes it possible to follow, in real time, the fixation of the molecules injected on the chip. Other instruments making it possible to measure the affinity and/or the avidity of an antibody for an antigen based on the plasmon resonance analysis are marketed, more particularly IASYS, OWLS, IBIS, TISPR-Spreeta Interactor/SPRiLab, SPRimager II (trade mark). ProteOn XPR36 (BIO-RAD) can also be mentioned.

More particularly, the biological molecule against which the antibody (autoantibody), the affinity and/or avidity of which is measured, is directed is (i) a neuropeptide, (ii) a hormone, or (iii) a neurotransmitter. The hormone is a peptide-like hormone. The same peptide-like molecule can also be called a neuropeptide or a hormone as a function of the origins or the site of action thereof. For example, the α-MSH or ghrelin secreted by the hypothalamic neurons are called neuropeptides, whereas the α-MSH secreted by the hypophysis or ghrelin secreted by the stomach are called hormones. Besides, α-MSH or ghrelin having a peripheral origin, but acting on neurons, can also be called hormones or neuropeptides.

According to a particular embodiment, the neuropsychiatric disease or the eating disorder is anorexia nervosa and the biological molecule is the alpha melanocyte stimulating hormone (α-MSH). According to another particular embodiment, the eating disorder is bulimia and the biological molecule is the alpha melanocyte stimulating hormone (α-MSH). According to still another particular embodiment, the disease is an eating disorder and the hormone is leptin. According to still another particular embodiment, the invention relates to a method making it possible to make a different diagnosis of EDs and other MBDs and neuropeptides or hormones against which the autoantibodies, the affinity and/or avidity of which is measured, are directed are: α-MSH, leptin, ghrelin, AgRP (Agouti-related peptide), NPY (Neuropeptide Y), MCH (Melanin-concentrating hormone), orexin (hypocretin, PYY (Peptide YY), galanin, ACTH (corticotropine) CRH (corticotropine-releasing hormone), ocytocin, vasopressin, gonadotropine and growth hormone.

According to a second aspect, MBDs are EDs such as anorexia nervosa, bulimia, eating disorders non otherwise specified, anxiety and depression, social phobia, delinquency, sexual disorders and sleep disorders, fibromyalgia, the irritable bowel syndrome, obesity by excessive caloric intake, complications caused by obesity, type II diabetes and the metabolic syndrome. According to still another particular embodiment, the invention relates to a method for diagnosing neuropsychiatric diseases included in the group comprising mood disorders, anxiety, more particularly social phobia, depression, memory impairment by (i) a measurement of the affinity and/or avidity of antibodies resulting from a biological sample directed against a neuropeptide, a hormone or a neurotransmitter chosen from the group consisting in corticotropine-releasing hormone or CRH, adrenocoticotropic hormone or ACTH, vasopressin, ocytocin, urocortins, then (ii) the comparison of the affinity value obtained with a control value.

According to another variant, the method makes it possible to diagnose neuropsychiatric diseases more particularly sexual disorders, sleep disorders, anxiety or an eating disorder by (i) the measurement of the affinity and/or avidity of antibodies resulting from a biological sample directed against the biological molecules selected from the group comprising peptides of the melanocortin family, AgRP (agouti-related peptide), neuropeptide Y (NPY), MCH hormone (melanin-concentrating hormone), galanin, hypocretin (orexin) or cocaine and amphetamine-regulated transcript (CART) then (ii) the comparison of the affinity value obtained with a control value. According to still another variant, the method makes it possible to diagnose neuropsychiatric diseases associated with somatic or visceral pains and anxiety in human beings by (i) measuring the affinity and/or the avidity of antibodies resulting from a biological sample directed against the biological molecules selected from the group comprising opioïd peptides, tachykinin peptides, ocytocin and peptides of the family of melanocortin then (ii) comparing the affinity value obtained with a control value. According to another variant, the method makes it possible to diagnose metabolic disorders and/or digestive functional disorders, the biological molecule being chosen from the group comprising somatostatin, GHRH hormone (growth hormone releasing hormone), TRH hormone (thyrotropine releasing hormone), GRH hormone (gonadotropine releasing hormone), adenohypophyseal hormones, insulin, glucagon, leptin, adiponectin, cytokine, peptides of the family of growth factors, vasoactive intestinal peptide (VIP), pituitary adenylate cyclase activating-peptide (PACAP), glucagon-like peptide (GLP), ghrelin, motilin, cholecystokinin, secretin, gastrin, oxyntomodulin, peptide YY, pancreatic peptide. In the present invention, type 1 diabetes is not considered as a metabolic disease.

According to a second aspect, the present invention relates to a diagnostic kit making it possible to implement the methods according to the invention which are described hereabove. This diagnostic kit contains (i) at least one biological molecule such as previously defined and will preferably contain (ii) at least one control sample, each control sample comprising an antibody directed against one of said biological molecules and the affinity against said biological molecule of which is known. The biological molecules can be present in the kit as fixed on a support, more particularly a matrix of the Biacore (trade mark) type "sensor chip" composed of a glass support cover functionalized with a biopolymer, carboxymethylated dextran, which makes it possible to use them to directly determine the affinity and/or avidity using a BIAcore (trade mark) device.

According to a third aspect of the present invention relates to compounds modulating the concentration of the complexes formed by (i) a biological molecule involved in the homeostasic regulation and/or the motivational behavior and/or in emotion and (ii) an antibody X directed against said biological molecule as a drug. The molecule involved in the homeostasic regulation in the motivational behavior and/or in the emotion can be more particularly a neuropeptide, a hormone or a neurotransmitter.

According to a first variant of this aspect of this invention, said compound modulates the affinity of the antibody X for said biological molecule. According to a second variant, said compound is a "decoy" molecule analogous to said biological molecule, more particularly an agonist, capable of forming a complex with the antibody X. According to another variant, said compound is an immunoglobulin or a fragment thereof, more particularly Fab and/or Fab' fragments, which has an affinity for said biological molecule which is greater than that of the antibody X for the same biological molecule, so that the immunoglobulin induces the dissociation of the antibody X involved in the antibody X/biological molecule complex by forming a new immunoglobulin/biological molecule complex. The association constant Ka which represents the affinity of the immunoglobulin is different from that of the antibody X by a factor of 10 to 10,000, preferably 100 to 1,000. According to another variant, said compound is an immunoglobulin or a fragment thereof, more particularly the Fab and/or Fab' fragments, which has an affinity for said biological molecule which is greater or smaller than that of the autoantibody X for the same biological molecule, so that the immunoglobulin reduces the formation of autoantibody X/biological molecule complexes by forming new immunoglobulin/biological molecule complexes. The association constant Ka which represents the affinity of immunoglobulin is different from that of the autoantibody X by a factor of 10 to 10,000, preferably 100 to 1,000.

More particularly, the therapeutic aspect of this invention relates to the utilization, for the treatment of NDs, MBDs and EDs, of immunoglobulins directed against specific neuropeptides. For example, for the therapy of anorexia nervosa, a disease which is characterised by the reduction in the affinity of IgM autoantibodies for α-MSH (refer to the example part), it would be necessary to give the patients immunoglobulin, preferably IgMs having an affinity for α-MSH which is stronger than the affinity of the patient's IgM autoantibodies. In each case of NDs, MBDs, EDs and metabolic diseases, the selection of the therapeutic immunoglobulins (nature of the Ig and/or the affinity) will be based on the results of the diagnostic tests described in the first part of this invention, by measuring the affinity of the autoantibodies directed against the neuropeptides/hormones to determine which peptidergic system is concerned.

According to the third aspect of the invention, the treatment of obesity can be mentioned, which uses compounds modulating the concentration of complexes formed by anti-ghrelin antibodies and ghrelin. As a matter of fact, a recent work shows that the immunization of rats with ghrelin fragments reduces obesity in rats (Zorilla and al., 2006). However, in this work, the authors do not think that the effect of immunization on the body weight can result from the modifications in the interactions between ghrelin and autoantibodies against ghrelin. As a matter of fact, the existence of autoantibodies against ghrelin in humans or in animals has not been reported in the prior art. The compounds according to this third aspect of the invention can be included in a composition further comprising pharmaceutically acceptable excipients or active principles admissible in pharmacy.

According to a fourth aspect, the invention relates to the utilization of compounds modulating the concentration of the complexes formed by (i) a biological molecule involved in the homeostasic regulation and/or the motivational behavior and/or in emotion and (ii) an antibody X directed against said biological molecule for the manufacturing of drugs intended for the treatment of neuropsychiatric diseases, eating disorders and/or metabolic diseases. Drugs can be intended for the treatment of EDs and MBDs. The diseases to be treated and the biological molecules according to this embodiment are identical to those detailed hereinunder in the part relating to diagnosis methods according to the first aspect of the invention.

The compounds according to this fourth aspect of the invention can be either:
(i) compounds modulating the affinity of the antibody X for said biological molecule; or
(ii) "decoy" molecules analogous to said biological molecule, more particularly agonists capable of forming a complex with the antibody X; or
(iii) one immunoglobulin or a fragment thereof (more particularly a Fab fragment and/or a Fab' fragment) which has an affinity for said biological molecule which is greater than that of the antibody X for the same biological molecule so that immunoglobulin induces the dissociation of the antibody X involved in the antibody X/biological molecule complex by forming an immunoglobulin/biological molecule complex; or
(iv) an immunoglobulin or a fragment thereof (more particularly a Fab fragment and/or a Fab' fragment) which has an affinity for said biological molecule which is greater or lower than that of the autoantibody X for the same biological molecule, so that the immunoglobulin reduces the formation of the autoantibody X complexes by forming a new immunoglobulin/biological molecule complex.

The association constant Ka which represents the affinity of immunoglobulin is different from that of the antibody X by a factor which can range from 10 to 10,000 and more particularly from 100 to 1,000. A variant of this aspect of the invention is the utilization of immunoglobulin or fragments thereof, specifically directed against neuropeptides, hormones or neurotransmitters the constant of affinity of which is known, for the production of a drug intended for the treatment of neuropsychiatric diseases, eating disorders and/or metabolic diseases.

A particular embodiment of the invention relates to the utilization of immunoglobulins or fragments thereof, more particularly IgGs, IgMs and/or IgAs having an affinity determined for the neuropeptide of α-MSH for example 500 to 1,500 resonance units measured by BIAcore for the IgMs, for the production of a drug intended for the treatment of anorexia nervosa. Values of equilibrium resonance units represent the relative affinity of the autoantibodies. Another particular embodiment relates to the utilization of immunoglobulin or a (Fab and/or Fab') fragment thereof having a strong affinity for α-MSH (500 to 1,500 RU) for the production of a drug intended for the treatment of anorexia nervosa.

Another particular embodiment relates to the utilization of immunoglobulins or a (Fab and/or Fab') fragment thereof with a physiological affinity for α-MSH (50 to 1,500 RU, for example 500 to 1,500 RU) for the production of the drug intended for the treatment of anorexia nervosa. The 500 to 1,500 RU affinity is considered as a strong affinity. It is appropriate for example for the IgMs. The physiological affinity is determined by the means values of the affinity measured in sound patients. An affinity between 50 (control patients) to 200 RU (bulimic patient value) is considered as low by the inventors of the present invention. It is appropriate for example for IgGs. These affinity values are convertible into conventional units by the BIAcore analysis of several dilutions of a sample, the autoantibodies concentration of which is known, followed by a transformation in Ka using for example "the BIAevaluation" (trade mark) (Biacore International AB, Uppsala, Sweden) software as described in detail in the article by Adamczyk M and al (Adamczyk and al., 2000).

According to this fourth aspect of the invention, the utilization of compounds modulating the concentration of complexes formed by anti-ghrelin autoantibodies and ghrelin for the production of a drug intended for the treatment of obesity can be mentioned. The utilization of compounds modulating the concentration of the complexes formed by anti-leptin antibodies and leptin for the production of a drug intended for the treatment of obesity can also be mentioned.

According to this fourth aspect of this invention drugs may further include pharmaceutically acceptable excipients or active principles admitted in pharmacy. Drugs can be in any form allowing an efficient administration of the active principle according to the invention. More particularly, they can be in a liquid form, in particular so as to be injected. They can also be in any other form allowing an injection. Such drugs can be solutions or emulsions. More particularly this is an aqueous solution.

The drug can further include at least one additive, more particularly selected from the group comprising:
one more particularly aqueous or non aqueous, hydrophilic or hydrophobic solvent;
a for example non ionic, anionic, cationic surfactant or a mixture of surfactants and more particularly a non ionic surfactant;

a chelating agent;
a preserver more particularly an antioxidant or an antimicrobial agent; and
a mixture thereof.

The delivery in a patient of such compounds as a drug, or drugs comprising such compounds, more particularly immunoglobulins having a determined affinity, can be made by passive (enteral or parental) administration or by active immunization either (i) with peptides specifically selected for their capacity to involve the production of immunoglobulins having the required affinity or (ii) DNAs, RNAs or derivatives thereof encoding said peptides. The subject of the invention will be better understood when reading the following examples given as illustrations and which are not limitative.

An example of the present invention is the identification of ED biomarkers such as anorexia nervosa of the restrictive type and anorexia nervosa of the mixed type with bulimia. Anorexia is considered as restrictive when the patient eats very little food, whereas anorexia is considered of a mixed type when the patient eats very little food and sometimes suffers from crises of bulimia often followed by vomiting.

The affinity of autoantibodies directed against α-MSH from a patient suffering of ED and from a sound patient has been determined. The autoantibodies directed against the neuropeptides/hormones can be isolated from blood and other human biological liquids. Any equipment especially designed for measuring chemical interaction forces between proteins and making it possible to express affinity values of a protein for the other, can be used in order to determine the affinity and/or the avidity of autoantibodies.

EXAMPLES

Example 1

In the experiment described hereinunder, the BIAcore technique has been used for determining the affinity of the autoantibodies.
The protocol used is as follows:
1. Separation of the serum by centrifuging blood from a part of patients suffering from ED and, on the other hand, from sound persons (2,000 g, 10 min., 4° C.);
2. Purification of total immunoglobulins G (IgG) on protein G/agarose from the serum (Sigma St. Louis, Mo., product code 07700);
3. Dialysis of purified total IgGs with phosphate buffered saline (PBS) through dialysis membranes (MWCO 6-8000, Spectrum lab Inc. Interchim, France);
4. Purification of immunoglobulins M (IgM) from the plasma (or the plasma after the separation of IgGs). Plasma is dialyzed through the dialysis membranes (MWCO 6-8000, Spectrum lab Inc. Interchim, France) against 1 liter of distilled water. When the precipitate appears in the membranes, the content thereof is centrifuged and the sediment containing the IgMs is diluted in a phosphate buffer, 0.2M NaCl;
5. Preparation of the matrix (Sensor chip CM5, Biacore Int. AB, Uppsala, Sweden) through the link with 35 μl of the α-MSH peptide (Bachem, Switzerland, product code H-1075) diluted to 1 mg/ml in a 10 mM sodium acetate buffer using a Kit for the Coupling of Amines (Biacore Int. AB, Uppsala, Sweden, Product code: BR-1000-50) which enables the equivalent immobilization of ligands carrying an amine primary group.
6. Measurement of the affinity of the α-MSH-linked autoantibodies by the injection in a Biacore device (Biacore Int. AB, Uppsala, Sweden) of 25 μl of each sample of total IgGs and purified IgMs.
7. Analysis of the results by comparing the affinity values ("RU"—resonance unit) between the patients suffering from EDs and sound patients (control);

The same protocol is valid for measuring the affinity of all the Ig classes, more particularly IgA, IgE, IgG and IgM, directed against other neuropeptides/hormones and in the case of other NDs, MBDs, EDs or metabolic diseases.

Figure 1:
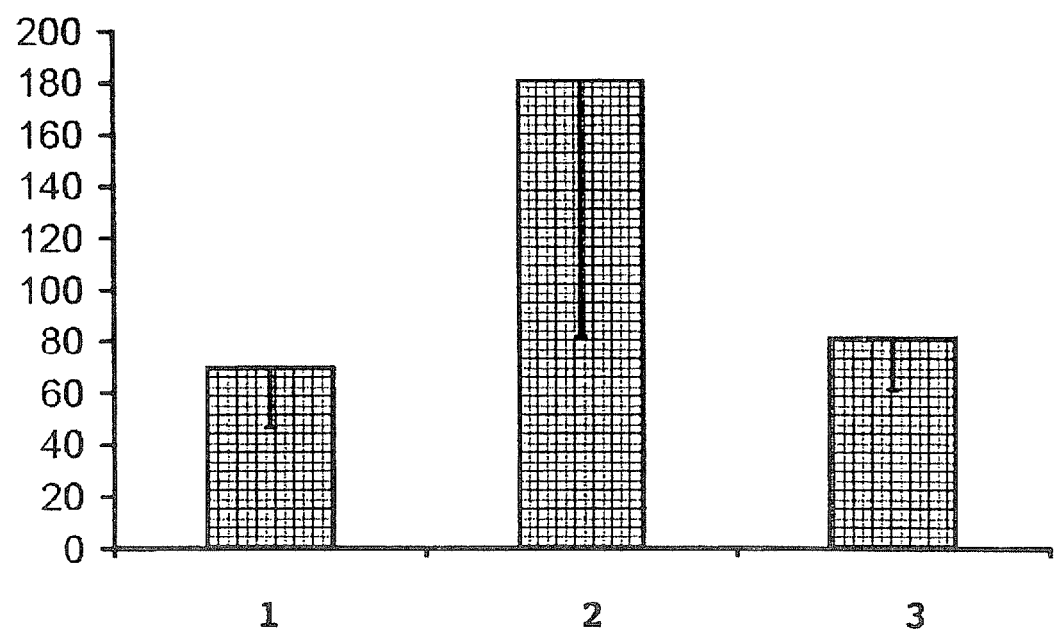
FIG. 1 is a histogram showing the affinity of IgG autoantibodies directed against α-MSH. The affinity is expressed in resonance units ("RU") which is an arbitrary unit used in the methods for measuring the affinity and/or avidity based on the study of plasmon resonance.
Figure 2:
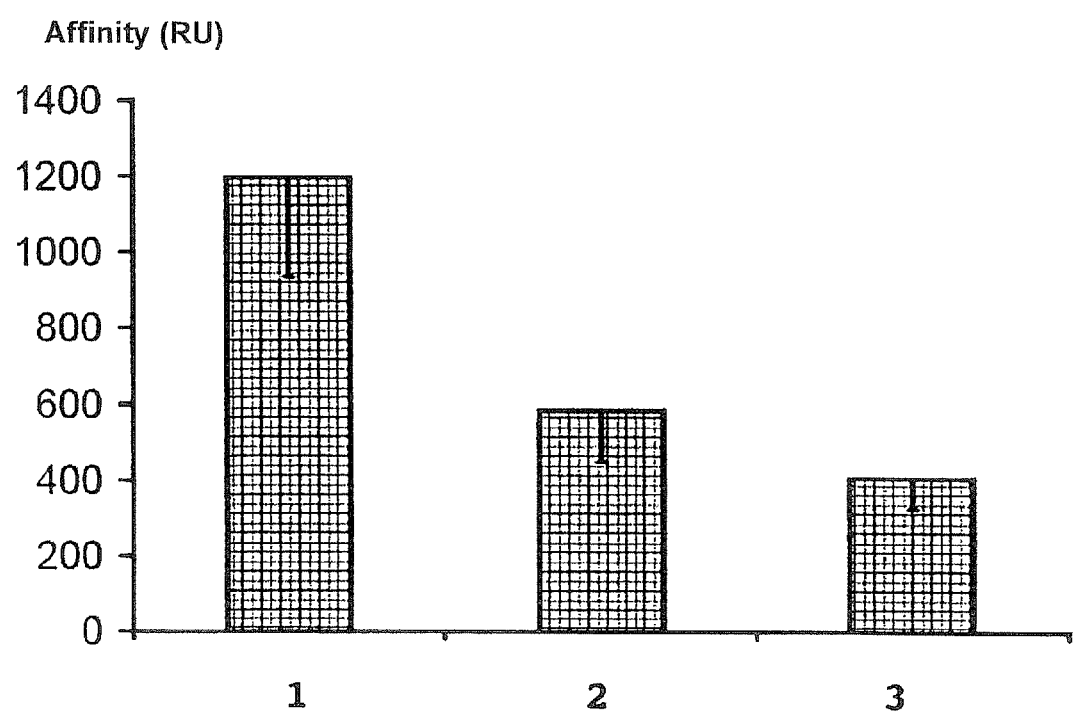
FIG. 2 is a histogram showing the affinity of IgM autoantibodies directed against α-MSH. The affinity is also expressed in resonance units ("RU").
Figure 3:
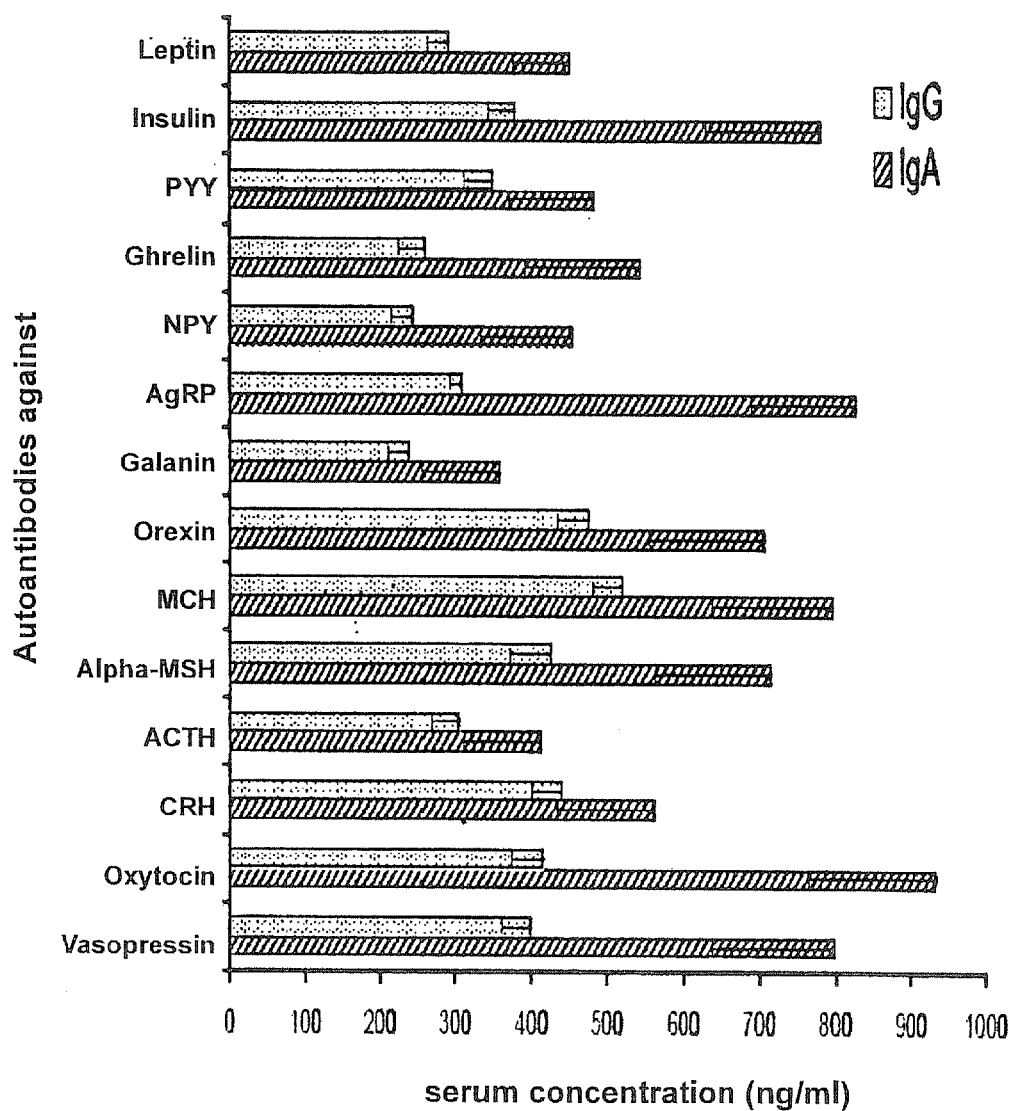
FIG. 3 is a histogram showing, in sound patients, the seruù concentrations expressed in ng/ml (average±SE) of the autoantibodies of the IgG and IgA types directed against fourteen neuropeptide/hormones measured with the direct ELISA technique described hereinunder for the α-MSH.

The results are shown in FIGS. 1 and 2. FIG. 1 is a histogram showing the affinity of the IgG autoantibodies directed against α-MSH. Column (1) shows the sound patients, column (2) shows the patients suffering from mixed anorexia and column (3) shows the patients suffering from restrictive anorexia.

FIG. 2 is a histogram shows the affinity of the IgM autoantibodies directed against α-MSH. Column (1) shows the sound persons, column (2) shows the persons suffering from mixed anorexia and column (3) shows the persons suffering from restrictive anorexia. The affinity is expressed in resonance units ("RU") which is an arbitrary unit used in the methods for measuring the affinity and/or the avidity based on the study of plasmon resonance.

The analysis of FIG. 1 shows that the increase in the affinity of the IgG autoantibodies directed against α-MSH is significantly associated with anorexia of the mixed type. As a matter of fact, the affinity of anti α-MSH IgGs present in patients suffering from mixed anorexia (column (2)) is significantly greater than that of anti α-MSH IgG autoantibodies present in sound persons (column (1)) and the persons suffering from restrictive anorexia (column (3)). In addition, the affinity of anti α-MSH IgG autoantibodies is similar in a sound person and a person suffering from restrictive anorexia (N=10, KRUkal-Wallis test p<0.01.*Dunn's post-hoc test p<0.05).

The analysis of FIG. 2 shows that the decrease in the affinity of IgM autoantibodies directed against α-MSH is significantly associated with anorexia of the mixed type and of the restrictive type (N=10, ANOVA p<0.05. *Tukey-Kramer post-hoc test p<0.05, a*T-test p<0.05). The affinity of the IgM autoantibodies from patients suffering from mixed anorexia or restrictive anorexia (respectively columns (2) and (3)) is significantly smaller than that of IgM autoantibodies present in sound patients (column (1)).

The method according to the invention thus makes it possible to determine that the increase in the affinity of the autoantibodies of the IgG (total) type is significantly associated with bulimia in patients suffering from anorexia of the mixed type (FIG. 1). Without being bound by a theoretical explanation, the increase in the affinity could result in a bulimia crisis by the rapid neutralization of α-MSH secreted during a meal, the α-MSH would thus no longer be able to fulfill its physiological action of inducing saturation and stopping dietary intake. In addition, the method according to the invention makes it possible to determine that the reduction in the affinity of autoantibodies of the IgM type directed against α-MSH is significantly associated with periods of anorexia in patients suffering from anorexia of the restrictive type or of the mixed type (FIG. 2). This reduction could be responsible for the failing elimination of α-MSH from circulation where this anorectic peptide is normally produced in a phasic way with the consequence of a permanent perception of saturation in patients suffering from anorexia.

The method according to the invention made it possible to determine that, after the extraction of the IgGs and the IgMs, the residual affinity of plasma for α-MSH is significantly high in female patients suffering from anorexia of the mixed type. This modification in the residual affinity is similar to the modification in the affinity noted for the IgGs. Thus, other classes of immuniglobulins have diagnostic values for NDs and EDs separately or in conjunction with the affinity values of the IgGs and/or the IgMs. More particularly, the IgAs directed against α-MSH or against other neuropeptides/hormones are present in sound persons or in persons suffering from EDs and have a diagnostic value. On the other hand, the affinity of autoantibodies is also responsible for the formation of immune complexes and can indirectly affect the balance between the level of free autoantibodies and the level of antigen-linked autoantibodies.

The presence of immune complexes between autoantibodies and neuropeptide/hormone affects the activity of this neuropeptide/hormone with the specific receptor thereof. The presence of immune complexes in a biological sample will limit or hinder the measurement of the affinity using the surface plasmon resonance technique for a neuropeptide/hormone having a certain quantity of autoantibodies which are already strongly linked with the antigen thereof in an immune complex.

The presence of immune complexes between antibodies and neuropeptide/hormone in a biological sample can be determined by measuring the ratio between free and linked antibodies (determination of the ratio of autoantibodies directed against free neuropeptides/hormones with respect to autoantibodies) as follows:
(i) execution of one ELISA with the dissociation of the antigen;
(ii) execution of a direct ELISA;
(iii) comparison of the results obtained in steps (i) and (ii) and determination of a percentage of autoantibodies which exist as immune complexes.

This method can have an additional diagnosing role with respect to the direct measurement of free autoantibodies. This method made it possible to determine that autoantibodies of the IgG (total) type capable of binding with α-MSH or with the growth hormone exist in immune complexes and at levels increasing in female patients suffering from anorexia nervosa of the restrictive type. The same method made it possible to determine the autoantibodies of the IgM type which can bind with α-MSH form immune complexes at reduced levels in patients suffering from anorexia of the restrictive type or of the mixed type. For the experiment mentioned hereabove, the ELISA technique was used to determine the levels of free or total antibodies which can bind with α-MSH.

A protocol which can be used for determining the percentage of autoantibodies present as immune complexes is as follows:
1. α-MSH peptide (Bachem, Switzerland, product code H-1075) was diluted to a concentration of 2 µg/ml in a 100 mM NaHCO3 buffer, pH 9.6 and coupled (100 µl per well) on 96-well microplates, Maxisorp (Nunc, Rochester, N.Y., United States) for 24 hours at 4° C.
2. After 3 washings for 5 minutes with a 0.05% PBS Tween 200 solution, pH 7.4, the plates were incubated overnight with a patient's plasma sample diluted (i) in a PBS buffer (1:100) to execute a direct ELISA or (ii) in a 3M NaCl, 1.5M Glycine buffer, pH 8.9 (1:200-1:1000) to execute one ELISA with the dissociation of immune complexes.
3. After 3 washings for 5 minutes with a 0.05% PBS Tween 200 solution, pH 7.4, the plates were incubated with rabbit antibodies (1:2000) directed against human IgGs conjugated with alkaline phosphatase (Jackson ImmunoResearch Laboratories Inc., West Grove, Pa.) for 3 hours at room temperature.
4. After 3 washings for 5 minutes with a 0.05% PBS Tween 200 solution, pH 7.4, the plates were incubated with 100 µl of p-nitrophenyl phosphate (Sigma, N2770) for 40 minutes at room temperature.
5. The reaction was stopped with 50 ml of 3N NaOH. The optical density was determined at 405 nm in a microplate reader.
6. A free antibodies/complex antibodies ratio was determined by dividing the values of optical densities obtained with the direct ELISA by the value of optical density obtained with ELISA with a dissociation. The higher the ratio, the fewer immune complexes were present.

Thus, the variation in the affinity or the avidity (which represents the total affinity) of the autoantibodies (more particularly IgGs, IgMs and/or IgAs) directed against α-MSH were identified as ED biological markers. The utilization of such markers in diagnosing EDs is justified by the important part of α-MSH in the regulation of appetite. This utilization is also justified by the results of an animal model of the passive transfer of autoantibodies against α-MSH as shown hereinunder. Even though the affinity of autoantibodies directed against α-MSH remained the key marker for EDs, it appears clearly that, owing to the multi-factor characteristics of EDs, these can be associated with the deregulation of other peptidergic systems than α-MSH in a varying way, depending on the patients.

Applying the same principles, variations of autoantibodies directed against other biological molecules more particularly neuropeptides/hormones will be identified as biological markers for other NDs as a function of a major part of each neuropeptide/hormone in homeostatic mechanisms, motivational behavior, emotion or metabolism. The modification in the affinity of autoantibodies is directed against vasopressin, ocytocin and ACTH as markers for depression or delinquency can be cited for example. The biological meaning of the changes affinity of autoantibodies directed against each neuropeptide/hormone separately or in a combination in NDs, EDs and metabolic diseases can thus be determined by applying the diagnosing methods according to the present invention.

In the initial phase of the development, diagnostic tests for NDs and EDs determining the affinity values will be used as pathological markers by comparison with the corresponding affinity values determined in sound patients. The detection of biological markers according to the present invention will enable the quick specific and non-equivocal diagnosis of NDs, EDs and metabolic diseases in patients requiring a specialized treatment which facilitates the utilization of an etiopathogenic therapeutic approach individually designed for each patient. In addition, the detection of such markers during the treatment of such NDs or EDs or metabolic diseases will favor the biological evaluation of the therapeutic efficiency of treatments and the evolution towards healing. Finally, the detection of such markers in persons suffering from beginning symptoms of NDs, EDs or MBDs or in persons coming from families suffering from NDs, EDs, MBDs will be able to help a precocious identification and treatment of these affections or even preventing the development thereof.

Example 2

To justify the new diagnosing concept of EDs by the measurement of the affinity of autoantibodies for neuropeptide/hormones involved in the regulation of motivational behavior, the inventors developed an experimental model of passive transfer in a rat of autoantibodies against α-MSH with a strong or a weak affinity. The autoantibodies of the IgG type were purified from the serum of patients suffering from anorexia nervosa or bulimia, the affinity of such IgGs for α-MSH was measured with the surface plasmon resonance technique (BiaCore) described in detail hereabove by showing the significantly higher values in patients suffering from bulimia (refer to FIG. 2 appended herewith). The IgGs from patients suffering from anorexia were grouped in one pool A, whereas the IgGs from patients suffering from bulimia were grouped in another pool B. The autoantibodies directed against α-MSH were purified from pool A and from pool B by the affinity against the α-MSH peptide on two chromatographic columns. The presence of the IgGs against α-MSH in the eluate was confirmed by the ELISA test. The IgGs directed against α-MSH were lyophilized and diluted in a buffer almost similar to the cerebro-spinal liquid with a final concentration of 3 mg/ml.

Wistar rats were anesthetized and implanted using a stereotaxic device with metallic canules (PlasticOne) targeting the ventro-basal part of the unilateral hypothalamus. One week after the implantation of canules, the rats (n=30) were divided into 3 groups having an equal weight in the various groups. The rats were on a diet restricting food which was accessible between 10 am. and 6 p.m. everyday and water was given ad libidum. Thirty minutes prior to the supply of food, the waking rats received injections in hypothalamus through the 1 microlitre canule a day for five days:
the first group of rats received purified IgGs from pool A,
the second group received purified IgGs from the pool B, and
the third group received the buffer alone.

Figure 4:
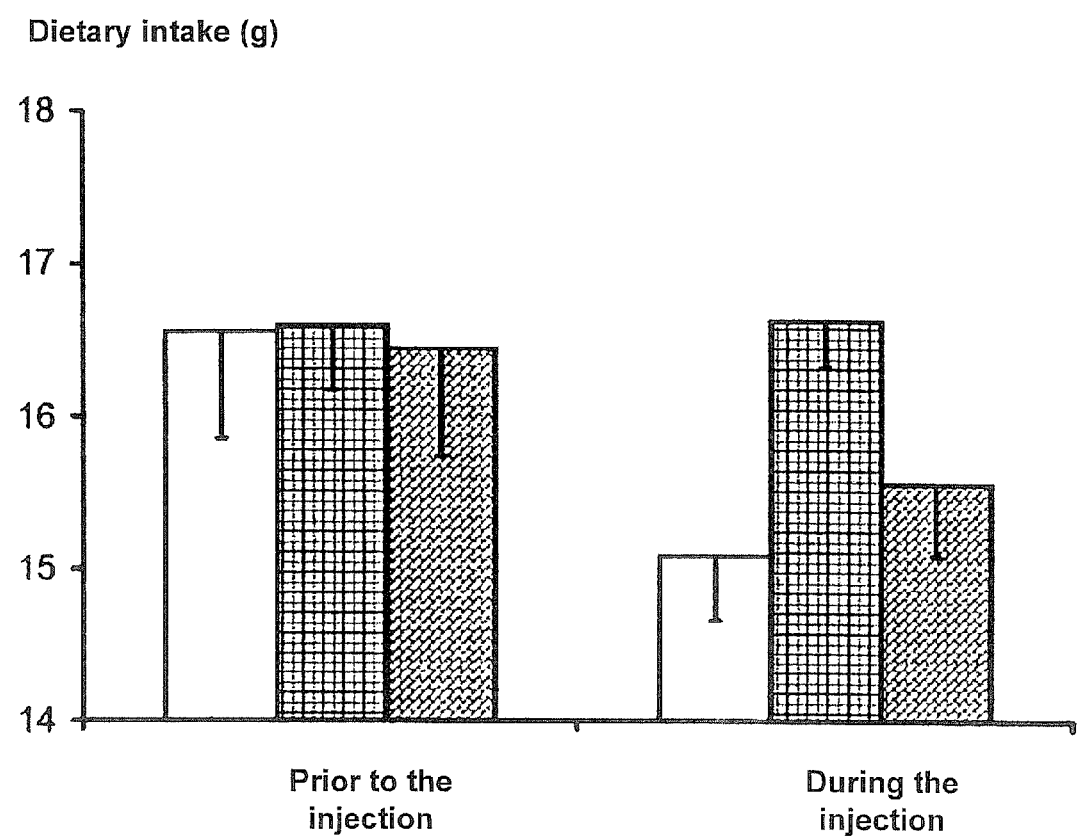
FIG. 4 is a histogram showing the dietary intake expressed in g (grams) (±SE) prior to an injection and during the injection of IgG in the experiments shown in example 2 hereinunder.
Figure 5:
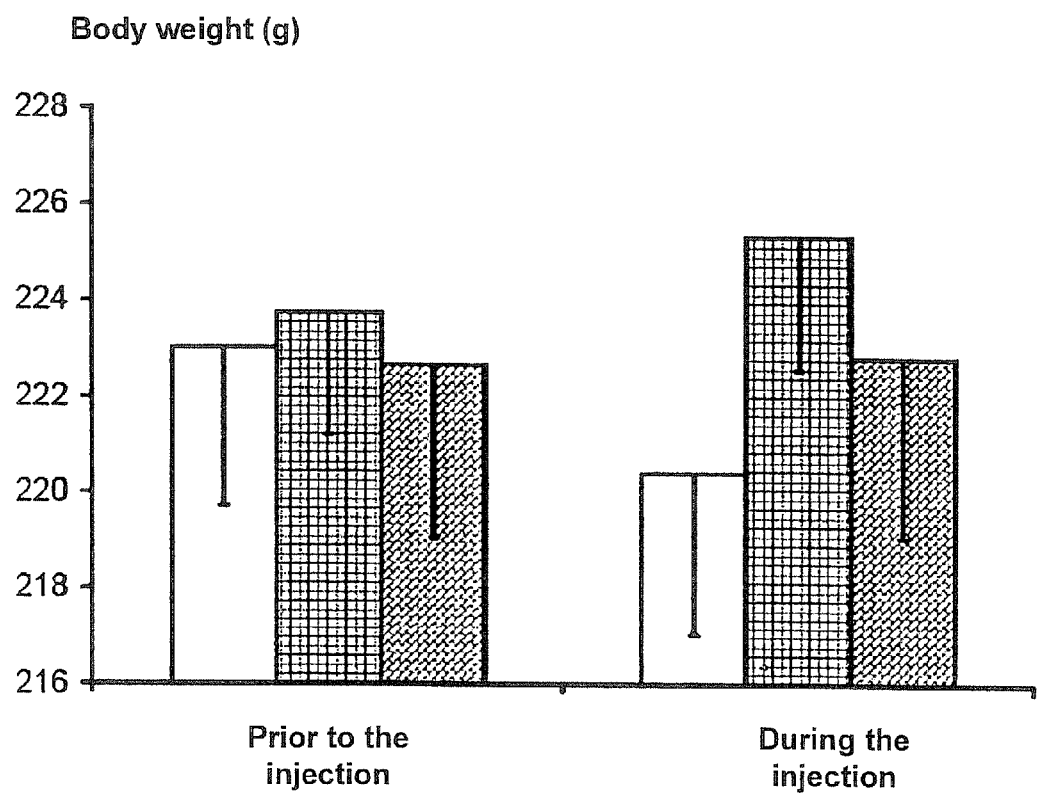
FIG. 5 is a histogram showing the dietary intake expressed in g (grams) (±SE) prior to an injection and during the intrahypotalamic injection of IgG.

The dietary intake and the body weight were measured everyday. The inventors noted that the rats injected with IgGs from pool B ate significantly more than the rats injected with IgGs from pool A, as shown in FIG. 4 appended herewith. This figure shows the dietary intake (g±SE) per day during the restriction:
the three columns on the left (consecutively from left to right, Pool A, Pool B and buffer alone, corresponding, prior to the injection into the hypothalamus;
the three columns on the right, the same groups during the injection.
KRUkal-Wallis test between groups during the injection, p=0.02, Dunn's test Pool A vs. Pool B p<0.05. In addition, the rats injected with IgGs from pool B gained body weight, whereas the rats injected with IgGs from pool A lost body weight with respect to a time prior to the injections, as shown in FIG. 5 appended hereto. FIG. 5 shows:
the gain in body weight (g±SE) during the restriction, respectively for the three columns on the left Pool A, Pool B and buffer alone, corresponding, prior to the injection into the hypothalamus;
the three columns on the right with the same groups during the injection. Match T-test: Pool A prior to vs. Pool A during the injection, p<0.01, Pool B prior to vs. during the injection p<0.05.
This experiment showed that:
(i) the functional importance causing the affinity of an autoantibody against a neuropeptide/hormone involved in the regulation of the motivational behavior such as α-MSH:
(ii) the possibility of modifying the dietary intake by changing the concentration in autoantibody against α-MSH.

It should however be noted that the injection into the brain of autoantibodies used in this experiment must be considered as an experiment model explaining action mechanisms of such autoantibodies on the dietary behavior, but not as a therapeutic way which must preferably use one of the peripheral ways.

References

1. Adamczyk M, Moore J A, Yu Z. 2000. Application of Surface Plasmon Resonance toward Studies of Low-Molecular-Weight Antigen-Antibody Binding Interactions. Methods 20:319-328.
2. Andlin-Sobocki P, Jonsson B, Wittchen H U, Olesen J. 2005. Cost of disorders of the brain in Europe. Eur J Neurol 12 Suppl 1:1-27.
3. Bendtzen K. et al., High-avidity autoantibodies to cytokines. Trends Immunology Today 19:5, 209-211, 1998.
4. Black J L, 3rd, Silber M H, Krahn L E, Fredrickson P A, Pankratz V S, Avula R, Walker D L, Slocumb N L. 2005. Analysis of hypocretin (orexin) antibodies in patients with narcolepsy. Sleep 28:427-431.
5. Choi Y H, Li C, Page K, Westby A, Della-Fera M A, Lin J, Hartzell D L, Baile C A. 2003. Melanocortin receptors mediate leptin effects on feeding and body weight but not adipose apoptosis. Physiol Behav 79:795-801.
6. Cone R D. 2005. Anatomy and regulation of the central melanocortin system. Nat Neurosci 8:571-578.
7. Comin R. et al. High affinity of anti GM1 antibodies is associated with disease onset in experimental neuropathy. J. Neurosci. Res. 84 :5, 1085-90, 2006.
8. Corcos M, Atger F, Levy-Soussan P, Avrameas S, Guilbert B, Cayol V, Jeammet P.1999. Bulimia nervosa and autoimmunity. Psychiatry Res 87:7782.
9. De Lecea L, Kilduff T S, Peyron C, Gao X, Foye P E, Danielson P E, Fukuhara C, Battenberg E L, Gautvik V T, Bartlett F S, 2nd, Frankel W N, van den Pol A N, Bloom F E, Gautvik K M, Sutcliffe J G. 1998. The hypocretins: hypothalamus-specific peptides with neuroexcitatory activity. Proc Natl Acad Sci USA 95:322-327.
10. de Wied D. 1969. Effects of peptide hormones on behavior. In: Ganong W F, Martini L, Editors. Frontiers in Neuroendocrinology. New York: Oxford University Press. p 97-140.
11. Dicou E. and Nerriére V., Evidence that natural autoantibodies against the nerve growth factor (NGF) may be potential carriers of NGF. Journal of Neuroimmunology, 75: 1-2, 200-203, 1997.
12. Fan W, Boston B A, Kesterson R A, Hruby V J, Cone R D. 1997. Role of melanocortinergic neurons in feeding and the agouti obesity syndrome. Nature 385:165-168.

13. Fetissov S O, Hallman J, Oreland L, af Klinteberg B, Grenbäck E, Hulting A L, Hökfelt T. 2002. Autoantibodies against a-MSH, ACTH, and LHRH in anorexia and bulimia nervosa patients. Proc Natl Acad Sci USA 99:1715517160.
14. Fetissov S O, Harro J, Jaanisk M, Järv A, Podar I, Allik J, Nilsson I, Sakthivel P, Lefvert AK, Hökfelt T. 2005. Autoantibodies against neuropeptides are associated with psychological traits in eating disorders. Proc Natl Acad Sci USA 102:14865-14870.
15. Fetissov S O, Hökfelt T. 2003. Autoimmune component in anorexia and bulimia nervosa. A new hypothesis for eating disorders. In: SSIB 11th Annual. Meeting. Groningen, The Netherlands.
16. Haller J, Mikics E, Halasz J, Toth M. 2005. Mechanisms differentiating normal from abnormal aggression: glucocorticoids and serotonin. Eur J Pharmacol 526:89-100.
17. Heisler L K, Cowley M A, Tecott L H, Fan W, Low M J, Smart J L, Rubinstein M, Tatro J B, Marcus J N, Holstege H, Lee C E, Cone R D, Elmquist J K. 2002. Activation of Central Melanocortin Pathways by Fenfluramine. Science 297:609-611.
18. Hökfelt T, Bartfai T, Bloom F. 2003. Neuropeptides: opportunities for drug discovery. Lancet Neurol 2:463-472.
19. Lawrence C B, Rothwell N J. 2001. Anorexic But Not Pyrogenic Actions of Interleukin-1 are Modulated by Central Melanocortin-3/4 Receptors in the Rat. Journal of Neuroendocrinology 13:490-495.
20. Leibowitz S F, Alexander J T. 1998. Hypothalamic serotonin in control of eating behavior, meal size, and body weight. Biological Psychiatry 44:851864.
21. Marks D L, Ling N, Cone R D. 2001. Role of the central melanocortin system in cachexia. Cancer Res 61:1432-1438.
22. Marsh D J, Hollopeter G, Huszar D, Laufer R, Yagaloff K A, Fisher S L, Burn P, Palmiter R D. 1999. Response of melanocortin-4 receptor-deficient mice to anorectic and orexigenic peptides. Nat Genet 21:119-122.
23. Meguid M M, Fetissov S O, Varma M, Sato T, Zhang L, Laviano A, RossiFanelli F. 2000. Hypothalamic dopamine and serotonin in the regulation of food intake. Nutrition 16:843-857.
24. Obici S, Feng Z, Tan J, Liu L, Karkanias G, Rossetti L. 2001. Central melanocortin receptors regulate insulin action. J. Clin. Invest. 108:1079-1085.
25. Pedrazzini T, Pralong F, Grouzmann E. 2003. Neuropeptide Y: the universal soldier. Cell Mol Life Sci 60:350-377.
26. Pinckard R N. 1978. Equilibrium dialysis and preparation of hapten conjugates. In: Weir D M, Editor. Handbook of experimental immunology. Oxford: Blackwell Science. p 17.11-17.23.
27. Rich R L, Myszka D G. 2000. Advances in surface plaimon resonance biosensor analysis. Current Opinion in Biotechnology 11:54-61.
28. Scantamburlo G, Hansenne M, Fuchs S, Pitchot W, Pinto E, Reggers J, Ansseau M, Legros J J. 2005. AVP- and OT-neurophysins response to apomorphine and clonidine in major depression. Psychoneuroendocrinology 30:839-845.
29. Seeley R J, Yagaloff K A, Fisher S L, Burn P, Thiele T E, van Dijk G, Baskin D G, Schwartz M W. 1997. Melanocortin receptors in leptin effects. Nature 390:349.
30. Sewards T V, Sewards M A. 2003. Fear and power-dominance motivation: proposed contributions of peptide hormones present in cerebrospinal fluid and plasma. Neuroscience & Biobehavioral Reviews 27:247-267.
31. Schlosser M. et al, In insulin-autoantibody-positive children from the general population, antibody affinity identifies those at high and low risk. Diabetologia 48: 1830-1832, 2005.
32. Swaab D F. 2004. Neuropeptides in hypothalamic neuronal disorders. Int Rev Cytol 240:305-375.
33. Tanaka S, Honda Y, Inoue Y, Honda M. 2006. Detection of autoantibodies against hypocretin, hcrtrI, and hcrtr2 in narcolepsy: anti-Hcrt system antibody in narcolepsy. Sleep 29:633-638.
34. Walsh B T, Kaplan A S, Attia E, Olmsted M, Parides M, Carter J C, Pike K M, Devlin M J, Woodside B, Roberto C A, Rockert W. 2006. Fluoxetine after weight restoration in anorexia nervosa: a randomized controlled trial. Jama 295: 2605-2612.
35. Zhang Y, Scarpace P J. 2006. Circumventing central leptin resistance: Lessons from central leptin and POMC gene delivery. Peptides 27:350-364.
36. Zorrilla E P, Iwasaki S, Moss J A, Chang J, Otsuji J, (noue K, Meijler M M, Janda K D. 2006. Vaccination against weight gain. Proc Natl Acad Sci USA. 29:12961-2.

The invention claimed is:
1. A method of diagnosing one of anorexia nervosa and bulimia in a human subject suspected of having such, the method comprising:
(i) measuring the affinity and/or the avidity of antibodies derived from a biological sample obtained from the subject, directed against alpha melanocyte stimulating hormone (α-MSH); and
(ii) comparing the affinity and/or the avidity value obtained with a control value to diagnose anorexia nervosa or bulimia in the subject.

* * * * *